US010503078B2

(12) United States Patent
Saraswatula et al.

(10) Patent No.: US 10,503,078 B2
(45) Date of Patent: Dec. 10, 2019

(54) CRITICALITY ANALYSIS AUGMENTED PROCESS WINDOW QUALIFICATION SAMPLING

(71) Applicant: KLA-TENCOR CORPORATION, Milpitas, CA (US)

(72) Inventors: Jagdish Chandra Saraswatula, Puttaparthi (IN); Saibal Banerjee, Fremont, CA (US); Ashok Kulkarni, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 113 days.

(21) Appl. No.: 15/903,841

(22) Filed: Feb. 23, 2018

(65) Prior Publication Data

US 2019/0072858 A1 Mar. 7, 2019

Related U.S. Application Data

(60) Provisional application No. 62/573,105, filed on Oct. 16, 2017.

(30) Foreign Application Priority Data

Sep. 1, 2017 (IN) .............................. 201741030977

(51) Int. Cl.
*G03F 1/84* (2012.01)
*G03F 7/20* (2006.01)
*G01N 21/956* (2006.01)
*H01L 21/66* (2006.01)

(52) U.S. Cl.
CPC .............. *G03F 7/7065* (2013.01); *G03F 1/84* (2013.01); *G01N 21/95607* (2013.01); *G03F 7/70666* (2013.01); *H01L 22/12* (2013.01)

(58) Field of Classification Search
CPC ...... G03F 7/7065; G03F 1/84; G03F 7/70666; G06T 7/0004; G01N 21/956; G01N 21/95607; H01L 22/12
USPC ....... 382/100, 141, 145, 149, 168, 170, 276, 382/286, 291, 305; 702/81, 33, 35, 121, 702/181, 82, 83, 127, 182, 183, 185; 700/90, 95, 108, 109, 110
See application file for complete search history.

(56) References Cited

U.S. PATENT DOCUMENTS

| 6,789,032 B2 * | 9/2004 | Barbour .................. G06F 17/18 702/121 |
| 6,902,855 B2 | 6/2005 | Peterson et al. |
| 7,418,124 B2 | 8/2008 | Peterson et al. |

(Continued)

OTHER PUBLICATIONS

ISA/KR, International Search Report and Written Opinion for PCT/US2018/048652 dated Dec. 13, 2018.

(Continued)

*Primary Examiner* — Sheela C Chawan
(74) *Attorney, Agent, or Firm* — Hodgson Russ LLP

(57) ABSTRACT

Techniques are provided that can select defects based on criticality of design pattern as well as defect attributes for process window qualification (PWQ). Defects are sorted into categories based on process conditions and similarity of design. Shape based grouping can be performed on the random defects. Highest design based grouping scores can be assigned to the bins, which are then sorted. Particular defects can be selected from the bins. These defects may be reviewed.

18 Claims, 4 Drawing Sheets

(56) References Cited

U.S. PATENT DOCUMENTS

| | | |
|---|---|---|
| 7,570,796 B2 | 8/2009 | Zafar et al. |
| 7,769,225 B2 | 8/2010 | Kekare et al. |
| 8,041,103 B2 | 10/2011 | Kulkarni et al. |
| 8,041,106 B2 | 10/2011 | Pak et al. |
| 8,213,704 B2 | 7/2012 | Peterson et al. |
| 2011/0172804 A1 | 7/2011 | Park et al. |
| 2015/0254832 A1 | 9/2015 | Plihal |
| 2016/0284579 A1 | 9/2016 | Kaizerman et al. |
| 2017/0186151 A1* | 6/2017 | Banerjee .............. G06T 7/0006 |

OTHER PUBLICATIONS

Nafisi et al., Improving Tool Efficiency through Automated Process Window Qualification 2010 IEEE/SEMI Advanced Semiconductor Manufacturing Conference (ASMC), Aug. 19, 2010, pp. 115-118.

\* cited by examiner

CRITICALITY ANALYSIS AUGMENTED PROCESS WINDOW QUALIFICATION SAMPLING

CROSS-REFERENCE TO RELATED APPLICATIONS

This application claims priority to the Indian patent application filed Sep. 1, 2017 and assigned application number 201741030977, and to the provisional patent application filed Oct. 16, 2017 and assigned U.S. App. No. 62/573,105, the disclosures of which are hereby incorporated by reference.

FIELD OF THE DISCLOSURE

This disclosure relates to review of semiconductor wafers.

BACKGROUND OF THE DISCLOSURE

As integrated circuit (IC) feature sizes shrink into the sub-wavelength regime, improved photolithography resolution increases frequency of yield impacting repeating defects from mask defects and resolution enhancements techniques (RET). Therefore, process window qualification (PWQ) to qualify a mask includes both mask inspection before wafer printing and wafer inspection after wafer printing.

Semiconductor device design and reticle manufacturing quality are verified by different procedures before the reticle enters a semiconductor fabrication facility to begin production of integrated circuits. The semiconductor device design is checked by software simulation to verify that all features print correctly after lithography in manufacturing. The reticle is inspected at the mask shop for reticle defects and measured to ensure that the features are within specification. Marginal RET designs not noted by simulation checks translate into electrical failures in wafer fabrication, affect yield, and possibly remain unnoticed until wafer fabrication is complete.

PWQ is a type of inspection performed on a specimen fabricated in a particular way that can check if a specific chip design can be manufactured (e.g., free of critical hot spots) and to decide about the optimal parameters for a lithography process (e.g., focus/exposure). Usually, a focus-exposure modulated specimen is printed to simulate different process window conditions. The specimen is then inspected using a relatively sensitive bright field (BF) inspection tool. The detected defects are divided into bins by a design-based algorithm that classifies the defects by type of printing error (a unique design structure is associated with each bin). To determine how a printing error is affecting the chip yield at different process modulations, a defect sampling strategy followed by scanning electron microscope (SEM) review is performed. For example, a few representative defects from each bin can be visited at different die modulations. This time-consuming procedure checks how a structure responds to changes in lithography parameters (focus/exposure) and finally the process window limits are determined. To increase sensitivity, a second iteration is sometimes performed. In that case, the previously identified printing errors can be used as care areas in the wafer inspection. The complete procedure may then be repeated.

The nature of PWQ is to induce pattern anomalies, such as transient repeating defects, by varying a process parameter or operating variable, such as focus, exposure, partial coherence of illumination, mode of illumination, or numerical aperture. Transient or "soft" repeating defects are defects that print under only specific conditions, such as, for example, defocus level, exposure dose, and photoresist uniformity conditions. The term "soft defects" also refers to defects that are cleanable, unlike "hard defects," in which the pattern is permanently cast in the reticle. The narrowing process window, which is primarily reduced depth of focus, is used to intentionally amplify any unexpected patterning behavior. The method increases the capture rate of pattern anomalies that sometimes depend on coincidental confluence of exposure, focus, illumination, and resolution enhancement technology patterning at the wafer plane.

The PWQ procedure can implement die-to-die inspection of a plurality of dies or other repetitive patterns on a semiconductor wafer or other substrate on which design patterns are printed by photoresist patterning performed in accordance with a lithographic process using either a single die reticle or a multi-die reticle. The procedure entails selecting an illumination operating variable to modulate. A layer of pattern recording material such as a photoresist covering a test wafer substrate is exposed in the form of a grid of regions arranged in rows and columns. The columns are arranged in a pattern of "A" columns representing regions exposed to different values of a predetermined operating variable and "B" columns representing regions exposed to a common reference value of the predetermined operating variable. Conventional inspection techniques identifying differences in the "A" regions compared with the "B" regions eliminate hard repetitive anomalies. Comparing differences between "A" region values for a given column relative to a reference value identifies transient repetitive anomalies. Each repetitive anomaly identified is evaluated for critical status. The procedure of comparing images formed by different values of a lithographic operating variable enables qualifying single die reticles and detecting design pattern defects. If the anomaly identified is of a design pattern type, critical status would depend on the number of occurrences and location of the anomaly on the design pattern.

The process or yield criticality information may include, for example, critical defects determined by PWQ, locations of defects of interest (DOI) based on hot spots (e.g., determined from inspection), hot spot information determined from logical bitmaps, a kill probability (KP) value determined from test results for a defect detected at a hot spot, any other process or yield information, or some combination thereof. A "hot spot" may be generally defined as a location in the design printed on the wafer at which a killer defect may be present. In contrast, a "cold spot" may be generally defined as a location in the design printed on the wafer at which a nuisance defect may be present. Data for the one or more attributes of the die image may also be referred to as "context" data that defines geometrical areas in the die image that have different values of one or more attributes. For example, this may include type(s) of features within the areas such as contact areas or dummy fill areas, "where to inspect" information or "care areas," "critical" areas in which a process failure is possible, or some combination thereof. The term context data is used interchangeably herein with the terms "context information" and "context map." The context information may be acquired from a variety of sources including simulation, modeling, and/or analysis software products that are commercially available from KLA-Tencor, other software such as design rule checking (DRC) software, or some combination thereof.

PWQ leverages the unique ability of lithography tools to modulate lithography exposure process parameters at the reticle shot level using focus and exposure as variables to determine design-lithography interactions. This application is often used for optical proximity correction (OPC) verification. However, PWQ is limited to the direct comparison of dies on a wafer that are printed with modulated focus and/or exposure parameters. The impact of other process variables associated with process steps such as etch, deposition, thermal processing, chemical-mechanical polishing (CMP), etc. cannot be directly assessed by PWQ since these variables can only be modulated at the wafer level.

PWQ sampling has been based on the qualitative assessment of an expert, such as an applications engineer, who would set up PWQ inspection recipe and would use a host of sampling mechanisms. These mechanisms include design based grouping (DBG) based sampling and process condition based sampling.

With DBG-based sampling, defect patterns based on an exact match are grouped into bins and the bins are prioritized based on the frequency of failing patterns. The bin with highest population is ranked highest. This method of sampling is based on design processing, but not design understanding. DBG-based sampling ignores criticality of patterns and sampling is done based on design based grouping ranks, which is population dependent.

With process condition based sampling for PWQ, the wafer map is laid out in a way that each die is uniquely modulated by focus or exposure. From each die, a few defects are sampled based on defect attributes generated by a broad band plasma (BBP) inspection tool. The design based attributes of process condition based sampling and diversity sampling do not consider design attributes. It has often been observed that high signal is detected from regions where there are no patterns in the immediate vicinity or are non-critical from process window (PW) perspective. Often these defects are referred to as an SEM non visuals (SNV). The signal could be coming from a layer below and may have no relevance to the layer being inspected. Thus, the SEM review may not find anything at that location.

Therefore, improved techniques for performing PWQ are needed.

BRIEF SUMMARY OF THE DISCLOSURE

In a first embodiment, a method is provided. Defects from a plurality of design based grouping bins are sorted into a plurality of categories based on a plurality of process conditions using a processor. The defects are sorted based on similarity of design into a plurality of bins using the processor. Each of the bins includes at least one of the design based grouping bins. A random defect is selected from the defects in each of the design based grouping bins using the processor. Shape based grouping is performed on each of the random defects using the processor. For each of the bins, one of the design based grouping bins with a score on an end of a range of scores after the shape based grouping is selected using the processor. This score may be a highest score or a lowest score. The respective score (e.g., the highest or lowest score) that was selected is assigned to each of the bins using the processor. The bins are sorted in order by the respective scores using the processor. Thus, the bins may be sorted in ascending or descending order. One of the defects with a highest defect attribute value is selected from each of the bins for each of the plurality of process conditions using the processor.

The method can further include performing a review of a wafer using a scanning electron microscope after selecting the defects with the highest defect attribute value.

The method can further include re-ordering, using the processor, the defects, the bins, and the design based grouping bins and repeating assigning of the respective score, sorting of the bins in order by the respective scores, and selecting one of the defects with the highest defect attribute value. The method also can further include performing a review of a wafer using a scanning electron microscope after selecting the defects with the highest defect attribute value.

The plurality of categories can include four of the categories.

The plurality of process conditions can include focus and exposure.

Sorting the defects based on similarity of the design can use a bin merge algorithm.

Prior to sorting the defects from the plurality of design based grouping bins, the method can further include grouping, using the processor, the defects into the design based grouping bins; consolidating, using the processor, the design based grouping bins into the bins; grouping, using the processor, the bins based on the plurality of process conditions; and determining, using the processor, dies that indicate an inflection in defect count.

In a second embodiment, a system is provided. The system comprises a processor in electronic communication with an electronic data storage unit and a wafer inspection tool. The processor is configured to perform the following steps. Defects from a plurality of design based grouping bins are sorted into a plurality of categories based on a plurality of process conditions. The defects are sorted based on similarity of design into a plurality of bins, wherein each of the bins includes at least one of the design based grouping bins. A random defect is selected from the defects in each of the design based grouping bins. Shape based grouping is performed on each of the random defects. For each of the bins, one of the design based grouping bins with a score on an end of a range of scores (e.g., a highest or lowest score) after the shape based grouping is selected. The respective score that was selected is assigned to each of the bins. The bins are sorted in order by the respective scores. One of the defects with a highest defect attribute value is selected from each of the bins for each of the plurality of process conditions.

The wafer inspection tool may be a scanning electron microscope.

The processor can be further configured to re-order the defects, the bins, and the design based grouping bins and repeat assigning the respective score, sorting the bins in order starting with the score, and selecting one of the defects with the highest defect attribute value.

Prior to sorting the defects from the plurality of design based grouping bins, the processor can be further configured to: group the defects into the design based grouping bins; consolidate the design based grouping bins into the bins; group the bins based on the plurality of process conditions; and determine dies that indicate an inflection in defect count.

In a third embodiment, a non-transitory computer-readable storage medium is provided. The non-transitory computer-readable storage medium comprises one or more programs for executing steps on one or more computing devices. The steps include sorting defects from a plurality of design based grouping bins into a plurality of categories based on a plurality of process conditions; sorting the defects based on similarity of design into a plurality of bins using a bin merge algorithm; selecting a random defect from the defects in each of the design based grouping bins; performing shape based grouping on each of the random defects; for each of the bins, selecting one of the design based grouping bins with a score on an end of a range of scores (e.g., a highest or lowest score) after the shape based grouping; assigning the respective score that was selected to each of the bins; sorting the bins in order by the respective scores; and selecting one of the defects with a highest defect attribute value from each of the bins for each of the plurality of process conditions. Each of the bins includes at least one of the design based grouping bins.

The steps can further include re-ordering the defects, the bins, and the design based grouping bins and repeating assigning the respective score, the sorting of the bins in order starting with the score, and selecting one of the defects with the highest defect attribute value.

The plurality of categories can include four of the categories.

The plurality of process conditions can include focus and exposure.

Sorting the defects based on similarity of the design can use a bin merge algorithm.

Prior to sorting the defects from the plurality of design based grouping bins the steps can further include: grouping the defects into the design based grouping bins; consolidating the design based grouping bins into the bins; grouping the bins based on the plurality of process conditions; and determining dies that indicate an inflection in defect count.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

Determination of the PW can be an important aspect of semiconductor chip manufacturing. The convoluted effects of focus and exposure of the photolithography scanner along with various other effects (e.g., overlay) acting in tandem may need to be understood to successfully manufacture integrated circuits in high volume. The entire manufacturing system may need to function within this PW to produce high yields. PWQ sampling has not been done based on an understanding of design weaknesses, which can improve results and, consequently, the manufacturing process.

It may be beneficial to have a larger process window with minimal critical dimension (CD) variation. Thus, three parameters that can form the basis of this analysis include focus, exposure, CD (e.g., failing repeaters, design), or overlay (e.g., showing how x and y pattern shifts cause defects).

PWQ can be improved by relating the design of failing patters with parameters like the focus, exposure, and shifts of the lithography scanner. Embodiments disclosed herein can provide a technique to discover this relationship based on pattern criticality ascertained by shape based grouping (SBG). This method can select defects based on criticality of design pattern as well as defect attributes. Results can be improved with the same sampling budget. The overall number of design based grouping bins also may be reduced.

Figure 1:
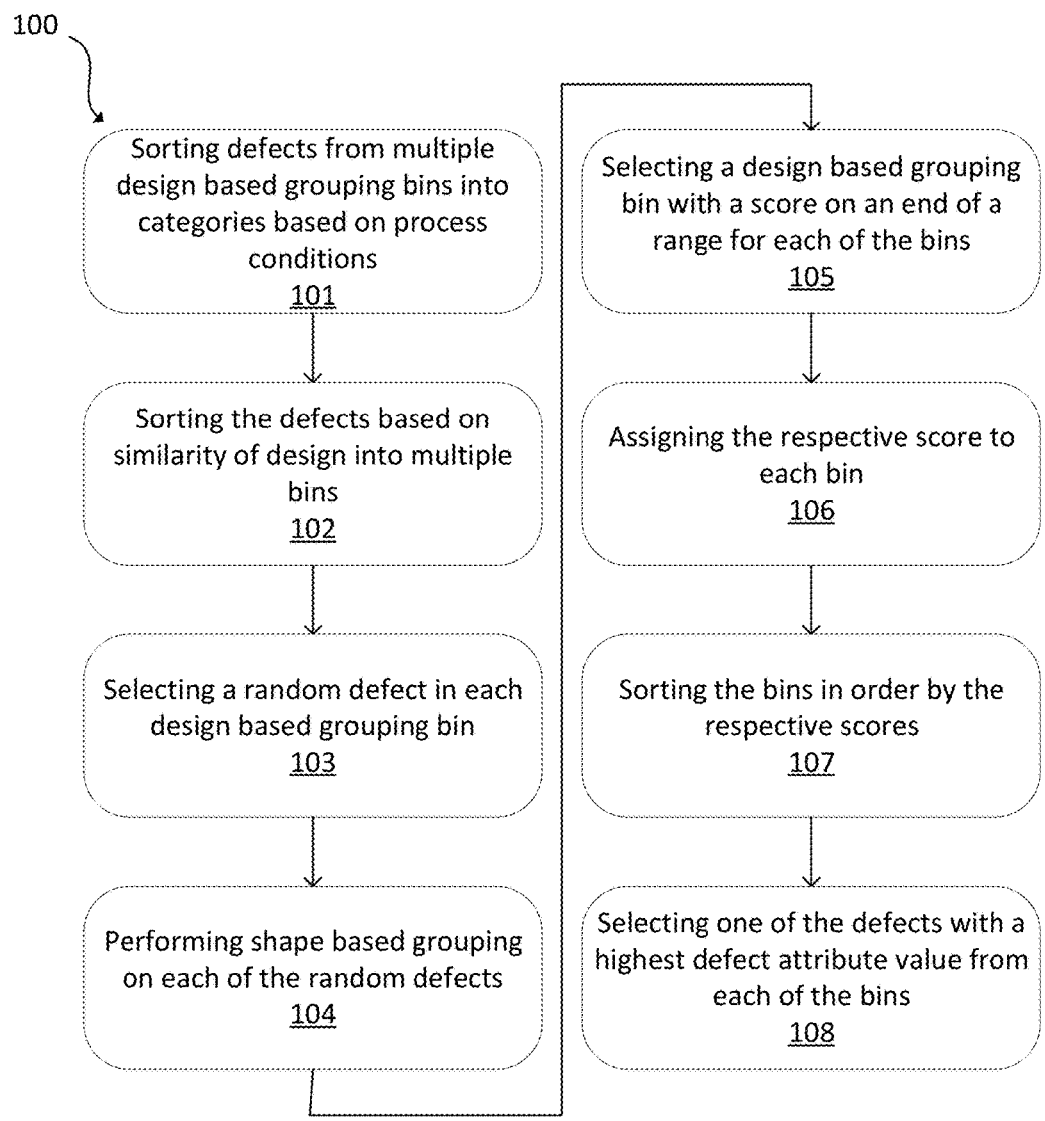
FIG. 1 is a flowchart of an embodiment of a method in accordance with the present disclosure.

FIG. 1 is a flowchart of an embodiment of a method 100. Each of the steps in the method 100 can be performed by a processor. The method 100 may be performed after an initial PWQ technique or can be performed independent of other PWQ techniques.

At 101, defects from a plurality of design based grouping bins can be sorted into a plurality of categories based on a plurality of process conditions. For example, four of the categories may be included. More or fewer categories also may be included. The plurality of process conditions can include focus and exposure. In an instance, the categories include +ve focus, −ve focus, +ve exposure, and −ve exposure. Other categories are possible.

The defects can be sorted at 102 into a plurality of bins based on similarity of design. Each of the bins can includes at least one design based grouping bin. Each of the bins may group multiple design based grouping bins together.

Sorting the defects based on similarity of the design in 102 may use a bin merge algorithm. Thus, the bins may be referred to as bin merge algorithm bins. A bin merge algorithm is a type of design based grouping.

Design based grouping employs an encoding scheme for each corner and surrounding geometry. This information is used to quickly find all patterns that exactly match a given pattern. This means that two locations are in a design based grouping group if their designs match exactly, and the design patterns of two locations that look similar but are numerically different even to a small extent fall into different groups. Design based grouping can include associating the defects with an underlying pattern whereby the defects with a same underlying pattern in a vicinity of the defects are in a same group.

All the defects for a given process condition can be considered. The bins may need to be sorted based on criticality of patterns because the defects are already grouped based on similarity of design.

A random defect can be selected from the defects in each of the design based grouping bins at 103.

Shape based grouping can be performed on each of the random defects at 104. Shape based grouping takes design clips as inputs and can give a score to each of the design clips citing the criticality of the clip as far as failure (e.g., defect) is concerned. Shape based grouping can use a fuzzy search based on probable defect causing mechanism. The embodiments disclosed herein can search for certain polygon combinations within a rule window. The regions marked by shape based grouping present a higher probability of defect occurrence. This provides at least two benefits. First, it can reduce nuisance by removing all those regions which have zero or low probability of failure. Second, it can minimize the location uncertainty by predicting the probable failure location.

For each of the bins, one of the design based grouping bins with a score on an end of a range of scores after the shape based grouping can be selected at 105. This score may be, for example, a highest score or a lowest score. Whether the score is a highest score or a lowest score may depend on the scoring methodology. The selected shaped based grouping score (e.g., the highest or lowest score) will become the score of that bin. For example, the highest shape based grouping score may be selected. Thus, the respective score that was selected can be assigned to each of the bins at 106. So the highest selected score can be assigned to the bin that includes the selected score. For example, scores can be generated by the bin merge algorithm or a shape based grouping algorithm. Each of the design clips is run (e.g., one per bin merge algorithm bin) and a score is generated.

While highest and lowest scores are disclosed, a score that is in, for example, the lowest 10% or the highest 90% may instead be selected.

At 107, the bins can be sorted in the bins in order by the respective scores. This may be in ascending or descending order. The scores can be the shaped based grouping score that was assigned in step 106.

One of the defects with a highest defect attribute value can be selected from each of the bins for each of the plurality of process conditions. In an instance, a defect with the highest defect attribute value from each of the bins for a given process condition can be selected. For example, a defect with the highest +ve focus can be selected. Defects can be selected for the remaining process conditions in a similar manner.

A review of a wafer can be performed after selecting the defects with the highest defect attribute value at 108. For example, a scanning electron microscope (SEM) can be used to perform the review.

After completing the method 100, the defects, the bins, and the design based grouping bins can optionally be re-ordered. Steps 106, 107, and 108 can be optionally repeated and a review of a wafer after selecting the defects with the highest defect attribute value can be performed, such as with an SEM.

For example, after completing one complete round of traversing through all the four process conditions, the defects, the bins, and the design based grouping bins can be re-ordered. Defects can be selected as described from steps 106, 107, and 108. In an instance, this process to select defects is repeated until a sampling budget is exhausted.

In an example, there are 100 defects on the wafer. The wafer inspection tool detects 200,000 events. This should be narrowed down to approximately 5,000 defects to verify using the SEM, and to try to find the 100 defects. Thus 5,000 defects are sampled from the reported 200,000 defects, which forms a sampling budget.

Figure 2:
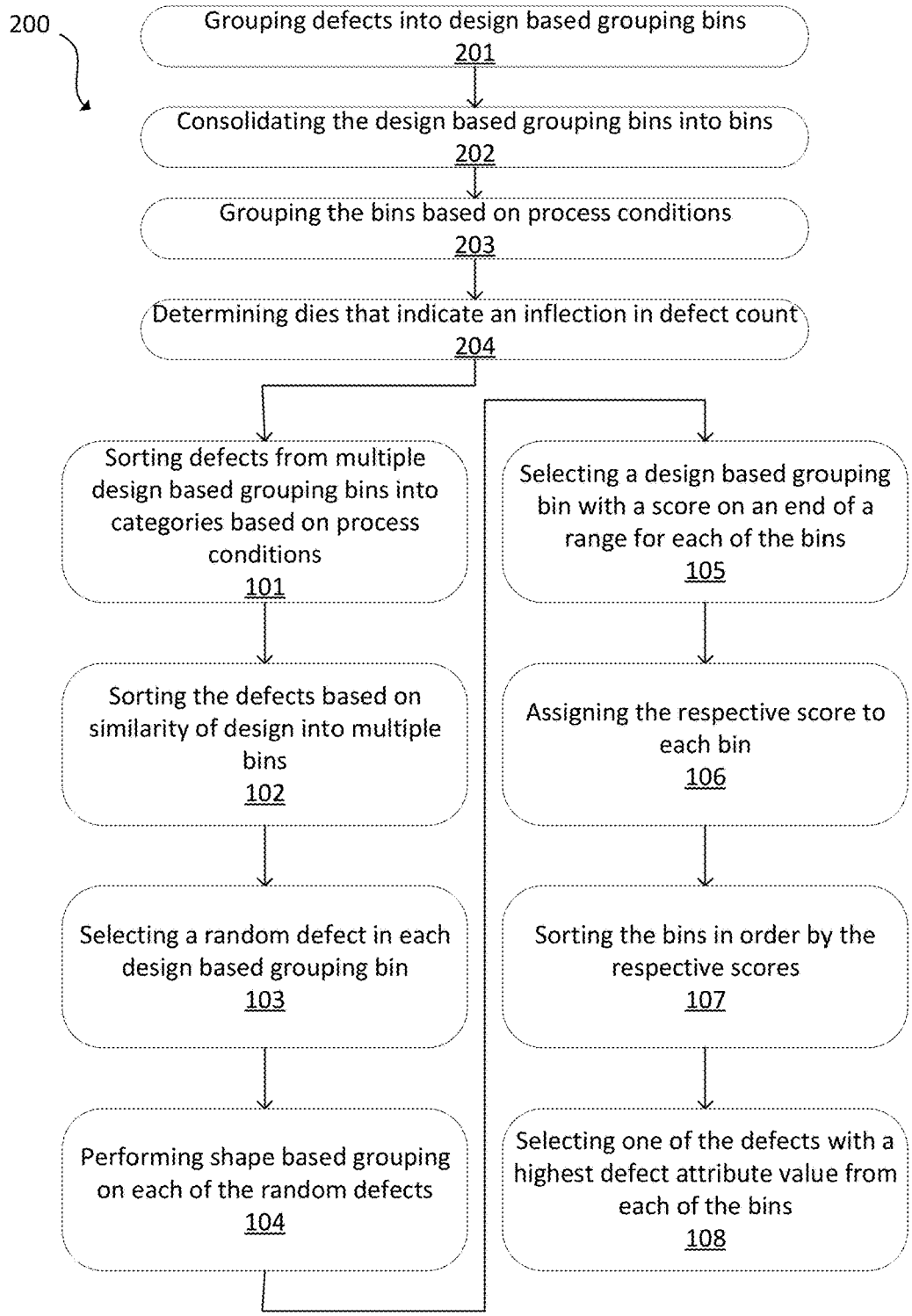
FIG. 2 is a flowchart of another embodiment of a method in accordance with the present disclosure.

FIG. 2 is a flowchart of another embodiment of a method 200. Prior to sorting the defects at 101, additional steps can optionally be performed. At 201, defects are grouped into design based grouping bins. The design based grouping bins can be consolidated into the bins (like the bin merge algorithm bins in 102) at 202.

The bins can be grouped based on the plurality of process conditions at 203. Dies that indicate an inflection in defect count are determined at 204. Then a review of a wafer can be performed after selecting the defects with the highest defect attribute value at 108. For example, an SEM can be used to perform the review.

Figure 3:
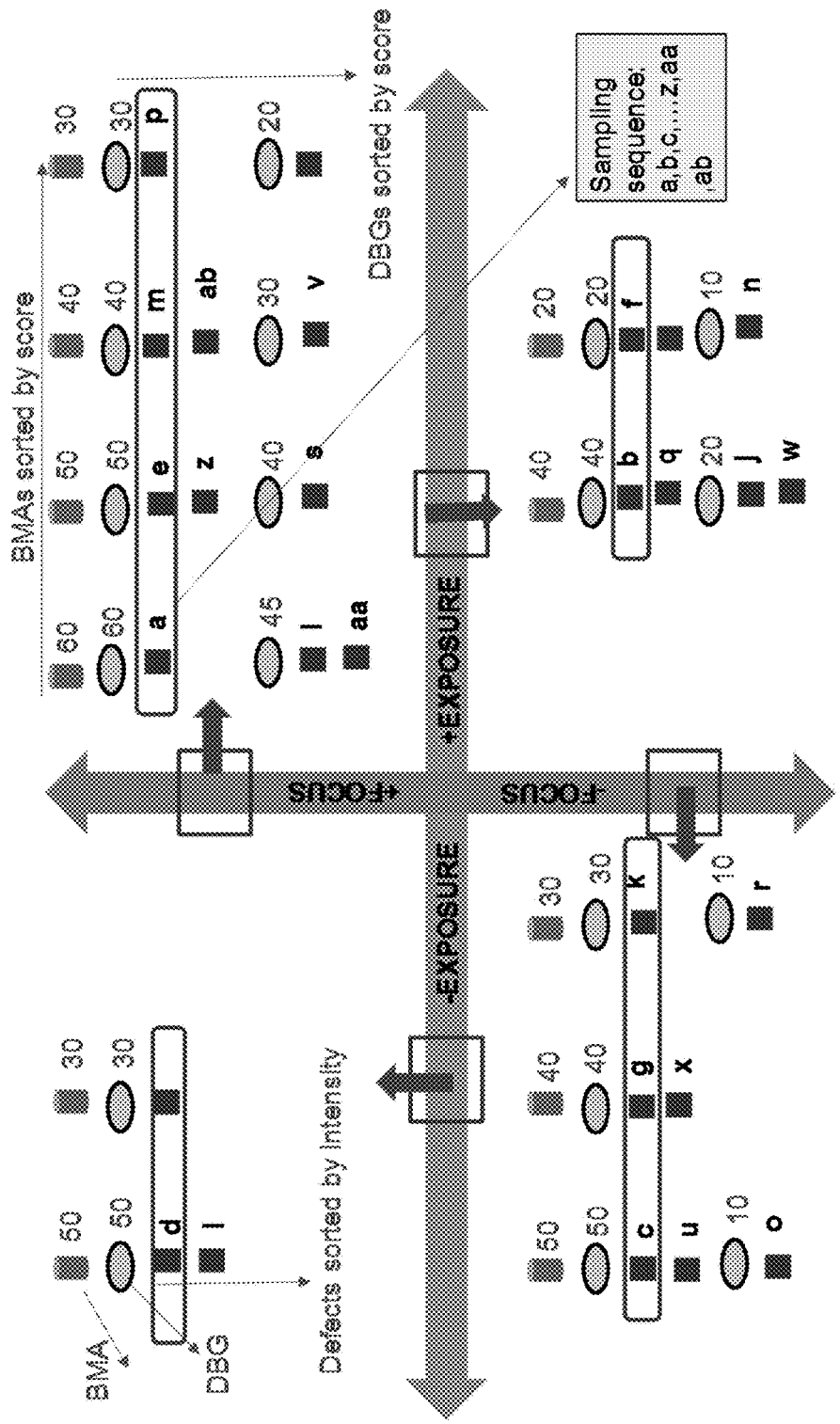
FIG. 3 is an exemplary diagram illustrating PWQ.

FIG. 3 is an exemplary diagram illustrating PWQ. This example shows modified round-robin sampling. FIG. 3 is a pictorial representation of step 101 of FIG. 1, which is sorting defects from a plurality of design based grouping bins into a plurality of categories based on a plurality of process conditions. Bins based on a bin merge algorithm (BMA) can be sorted, as seen in FIG. 3.

Other implementations of the present invention are methods of qualifying masks, reticles, or other patterns characterized by databases on which are stored image data acquired by practice of aerial image measurement system (AIMS) or design rule checking (DRC) techniques. In the case of AIMS, the stored image data are acquired by processing multiple aerial images of the reticle. In the case of DRC, the stored image data are acquired by simulation of the reticle design pattern.

Figure 4:
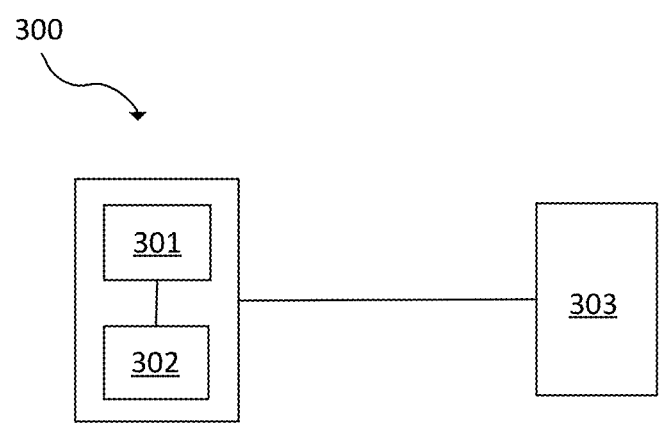
FIG. 4 is a block diagram of a system embodiment in accordance with the present disclosure.

FIG. 4 is a block diagram of a system embodiment. The system 300 includes a processor 301 and an electronic storage unit 302 in electronic communication with the processor 301. Both the processor 301 and the electronic storage unit 302 are in electronic communication with the wafer inspection tool 303. The processor 301 may include a microprocessor, a microcontroller, or other devices. A wafer inspection tool 303, which may be an optical inspection tool, can generate information used by the processor 301, such as design clips from bin merge algorithm or design based grouping bins. In an instance, the wafer inspection tool 303 is an SEM. The processor 301 and/or the electronic storage unit 302 optionally may be in electronic communication with a wafer metrology tool (not illustrated) to receive additional information.

The processor 301 and electronic storage unit 302 may be part of the wafer inspection tool 303 or another device. In an example, the processor 301 and electronic storage unit 302 may be part of a standalone control unit or in a centralized quality control unit. Multiple processors 201 or electronic storage unit 302 may be used.

The processor 301 may be implemented in practice by any combination of hardware, software, and firmware. Also, its functions as described herein may be performed by one unit, or divided up among different components, each of which may be implemented in turn by any combination of hardware, software and firmware. Program code or instructions for the processor 301 to implement various methods and functions may be stored in readable storage media, such as a memory in the electronic storage unit 302 or other memory.

The processor 301 may be coupled to the components of the system 300 in any suitable manner (e.g., via one or more transmission media, which may include wired and/or wireless transmission media) such that the processor 301 can receive output. The processor 301 may be configured to perform a number of functions using the output.

The processor 301, other system(s), or other subsystem(s) described herein may be part of various systems, including a personal computer system, image computer, mainframe computer system, workstation, network appliance, internet appliance, or other device. The subsystem(s) or system(s) may also include any suitable processor known in the art, such as a parallel processor. In addition, the subsystem(s) or system(s) may include a platform with high speed processing and software, either as a standalone or a networked tool.

If the system includes more than one subsystem, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

An additional embodiment relates to a non-transitory computer-readable medium storing program instructions executable on a processor for performing PWQ, as disclosed herein. In particular, the processor 301 can be coupled to a memory in the electronic storage unit 302 or other electronic data storage medium with non-transitory computer-readable medium that includes program instructions executable on the processor 301. The computer-implemented method may include any step(s) of any method(s) described herein. For example, the processor 301 may be programmed to perform some or all of the steps of FIG. 1, FIG. 2, or other embodiments disclosed herein.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes (MFC), SSE (Streaming SIMD Extension), or other technologies or methodologies, as desired.

In an instance, the processor 301 is configured to: sort defects from a plurality of design based grouping bins into a plurality of categories based on a plurality of process conditions; sort the defects based on similarity of design into a plurality of bins, wherein each of the bins includes at least one design based grouping bin; select a random defect from the defects in each of the design based grouping bins; perform shape based grouping on each of the random defects; for each of the bins, select one of the design based grouping bins with a score on an end of a range of scores after the shape based grouping (e.g., a highest or lowest score); assign the respective score that was selected to each of the bins; sort the bins in the bins in order by the respective scores; and select one of the defects with a highest defect attribute value from each of the bins for each of the plurality of process conditions.

In an instance, the processor 301 is further configured to: re-order the defects, the bins, and the design based grouping bins; and repeat assigning the respective score, sorting the bins in order by the respective scores, and selecting one of the defects with the highest defect attribute value.

In an instance, prior to sorting the defects from the plurality of design based grouping bins, the processor 301 can be further configured to: group the defects into the design based grouping bins; consolidate the design based grouping bins into the bins; group the bins based on the plurality of process conditions; and determine dies that indicate an inflection in defect count.

Program instructions implementing methods such as those described herein may be stored on computer-readable medium, such as in the electronic storage unit 302 or other storage medium. The computer-readable medium may be a storage medium such as a magnetic or optical disk, a magnetic tape, or any other suitable non-transitory computer-readable medium known in the art. For example, the memory in the electronic storage unit 302 or other electronic data storage medium may be a storage medium such as a magnetic or optical disk, a magnetic tape, or any other suitable non-transitory computer-readable medium known in the art. In particular, the electronic data storage unit 302 can include persistent storage, random access memory, or a split database.

In an instance, the non-transitory computer-readable storage medium, comprising one or more programs for executing the following steps on one or more computing devices. The steps on the non-transitory computer-readable storage medium can include sorting defects from a plurality of design based grouping bins into a plurality of categories based on a plurality of process conditions; sorting the defects based on similarity of design into a plurality of bins using a bin merge algorithm, wherein each of the bins includes at least one design based grouping bin; selecting a random defect from the defects in each of the design based grouping bins; performing shape based grouping on each of the random defects; for each of the bins, selecting one of the design based grouping bins with a score on an end of a range of scores (e.g., a highest or lowest score) after the shape based grouping; assigning the respective score that was selected to each of the bins; sorting the bins in order by the respective scores; and selecting one of the defects with a highest defect attribute value from each of the bins for each of the plurality of process conditions. For example, there may be four of the categories. The plurality of process conditions can include focus and exposure. Sorting the defects based on similarity of the design can use a bin merge algorithm.

The steps on the non-transitory computer-readable storage medium can further include re-ordering the defects, the bins, and the design based grouping bins; and repeating assigning the respective score, sorting of the bins in order, and selecting one of the defects with the highest defect attribute value.

Prior to sorting the defects from the plurality of design based grouping bins, the steps on the non-transitory computer-readable storage medium can further include: grouping the defects into the design based grouping bins; consolidating the design based grouping bins into the bins; grouping the bins based on the plurality of process conditions; and determining dies that indicate an inflection in defect count.

Each of the steps of the method may be performed as described herein. The methods also may include any other step(s) that can be performed by the processor and/or computer subsystem(s) or system(s) described herein. The steps can be performed by one or more computer systems, which may be configured according to any of the embodiments described herein. In addition, the methods described above may be performed by any of the system embodiments described herein.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. A method comprising:
    sorting, using a processor, defects from a plurality of design based grouping bins into a plurality of categories based on a plurality of process conditions;
    sorting, using the processor, the defects based on similarity of design into a plurality of bins, wherein each of the bins includes at least one of the design based grouping bins;
    selecting, using the processor, a random defect from the defects in each of the design based grouping bins;
    performing, using the processor, shape based grouping on each of the random defects;
    for each of the bins, selecting, using the processor, one of the design based grouping bins with a score on an end of a range of scores after the shape based grouping, wherein the score is a highest score or a lowest score;

assigning, using the processor, the respective score that was selected to each of the bins;
sorting, using the processor, the bins in order by the respective scores; and
selecting, using the processor, one of the defects with a highest defect attribute value from each of the bins for each of the plurality of process conditions.

2. The method of claim 1, further comprising performing a review of a wafer using a scanning electron microscope after selecting the defects with the highest defect attribute value.

3. The method of claim 1, further comprising:
re-ordering, using the processor, the defects, the bins, and the design based grouping bins; and
repeating assigning the respective score, sorting of the bins in order starting with the score, and selecting one of the defects with the highest defect attribute value.

4. The method of claim 3, further comprising performing a review of a wafer using a scanning electron microscope after selecting the defects with the highest defect attribute value.

5. The method of claim 1, wherein the plurality of categories includes four of the categories.

6. The method of claim 1, wherein the plurality of process conditions include focus and exposure.

7. The method of claim 1, wherein sorting the defects based on similarity of the design uses a bin merge algorithm.

8. The method of claim 1, wherein prior to sorting the defects from the plurality of design based grouping bins the method further comprises:
grouping, using the processor, the defects into the design based grouping bins;
consolidating, using the processor, the design based grouping bins into the bins;
grouping, using the processor, the bins based on the plurality of process conditions; and
determining, using the processor, dies that indicate an inflection in defect count.

9. A system comprising:
a processor in electronic communication with an electronic data storage unit and a wafer inspection tool, wherein the processor is configured to:
sort defects from a plurality of design based grouping bins into a plurality of categories based on a plurality of process conditions;
sort the defects based on similarity of design into a plurality of bins, wherein each of the bins includes at least one of the design based grouping bins;
select a random defect from the defects in each of the design based grouping bins;
perform shape based grouping on each of the random defects;
for each of the bins, select one of the design based grouping bins with a score on an end of a range of scores after the shape based grouping, wherein the score is a highest score or a lowest score;
assign the respective score that was selected to each of the bins;
sort the bins in order by the respective scores; and
select one of the defects with a highest defect attribute value from each of the bins for each of the plurality of process conditions.

10. The system of claim 9, wherein the wafer inspection tool is a scanning electron microscope.

11. The system of claim 9, wherein the processor is further configured to:
re-order the defects, the bins, and the design based grouping bins; and
repeat assigning the respective score, sorting of the bins in order starting with the score, and selecting one of the defects with the highest defect attribute value.

12. The system of claim 9, wherein prior to sorting the defects from the plurality of design based grouping bins the processor is further configured to:
group the defects into the design based grouping bins;
consolidate the design based grouping bins into the bins;
group the bins based on the plurality of process conditions; and
determine dies that indicate an inflection in defect count.

13. A non-transitory computer-readable storage medium, comprising one or more programs for executing the following steps on one or more computing devices:
sorting defects from a plurality of design based grouping bins into a plurality of categories based on a plurality of process conditions;
sorting the defects based on similarity of design into a plurality of bins using a bin merge algorithm, wherein each of the bins includes at least one of the design based grouping bins;
selecting a random defect from the defects in each of the design based grouping bins;
performing shape based grouping on each of the random defects;
for each of the bins, selecting one of the design based grouping bins with a score on an end of a range of scores after the shape based grouping, wherein the score is a highest score or a lowest score;
assigning the respective score that was selected to each of the bins;
sorting the bins in order by the respective scores; and
selecting one of the defects with a highest defect attribute value from each of the bins for each of the plurality of process conditions.

14. The non-transitory computer-readable storage medium of claim 13, wherein the steps further include:
re-ordering the defects, the bins, and the design based grouping bins; and
repeating assigning the respective score, sorting of the bins in order starting with the score, and selecting one of the defects with the highest defect attribute value.

15. The non-transitory computer-readable storage medium of claim 13, wherein the plurality of categories includes four of the categories.

16. The non-transitory computer-readable storage medium of claim 13, wherein the plurality of process conditions include focus and exposure.

17. The non-transitory computer-readable storage medium of claim 13, wherein sorting the defects based on similarity of the design uses a bin merge algorithm.

18. The non-transitory computer-readable storage medium of claim 13, wherein prior to sorting the defects from the plurality of design based grouping bins the steps further include:
grouping the defects into the design based grouping bins;
consolidating the design based grouping bins into the bins;
grouping the bins based on the plurality of process conditions; and
determining dies that indicate an inflection in defect count.

* * * * *